United States Patent
Moon et al.

(10) Patent No.: US 8,683,847 B2
(45) Date of Patent: Apr. 1, 2014

(54) MICROELECTROMECHANICAL SYSTEMS TYPE SEMICONDUCTOR GAS SENSOR USING MICROHEATER HAVING MANY HOLES AND METHOD FOR MANUFACTURING THE SAME

(75) Inventors: Seung Eon Moon, Daejeon (KR); Jae Woo Lee, Daejeon (KR); Nak Jin Choi, Daejeon (KR); Hyung Kun Lee, Daejeon (KR); Woo Seok Yang, Daejeon (KR); Jong Dae Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 304 days.

(21) Appl. No.: 13/345,772

(22) Filed: Jan. 9, 2012

(65) Prior Publication Data
US 2012/0198918 A1 Aug. 9, 2012

(30) Foreign Application Priority Data

Feb. 9, 2011 (KR) .................. 10-2011-0011436
Jul. 12, 2011 (KR) .................. 10-2011-0068818

(51) Int. Cl.
*H01L 21/02* (2006.01)
*G01N 7/04* (2006.01)

(52) U.S. Cl.
USPC .......................... 73/31.06; 438/53

(58) Field of Classification Search
None
See application file for complete search history.

(56) References Cited

U.S. PATENT DOCUMENTS

| | | | | |
|---|---|---|---|---|
| 3,505,180 A | * | 4/1970 | Brogden | 205/170 |
| 5,282,948 A | * | 2/1994 | Cole et al. | 204/421 |
| 5,321,983 A | * | 6/1994 | Nagata | 73/204.18 |
| 5,377,527 A | * | 1/1995 | Kamiunten | 73/25.03 |
| 5,834,777 A | * | 11/1998 | Wong | 250/343 |
| 6,541,676 B1 | * | 4/2003 | Franz et al. | 585/250 |
| 6,753,036 B2 | * | 6/2004 | Jankowski et al. | 427/189 |
| 6,810,899 B2 | * | 11/2004 | Franz et al. | 137/79 |

(Continued)

FOREIGN PATENT DOCUMENTS

| | | |
|---|---|---|
| JP | 2002-014076 A | 1/2002 |
| KR | 10-2003-0080833 A | 10/2003 |
| KR | 10-2005-0084980 A | 8/2005 |

OTHER PUBLICATIONS

Han Ji-Song; Tan Zhi-Yong; Sato, K.; Shikida, M., "Thermal-type micro sensor array on PI film substrate having wet-etched through-holes for interconnection," Transducers, Solid-State Sensors, Actuators and Microsystems, 12th International Conference on, pp. 1614,1617 vol. 2, Jun. 8-12, 2003.*

(Continued)

*Primary Examiner* — Lisa Caputo
*Assistant Examiner* — Punam Roy
(74) *Attorney, Agent, or Firm* — Rabin & Berdo, P.C.

(57) ABSTRACT

Disclosed are an MEMS type semiconductor gas sensor using a microheater having many holes and a method for manufacturing the same. The MEMS type semiconductor gas sensor includes: a substrate of which a central region is etched with a predetermined thickness; a second membrane formed at an upper portion of the central region of the substrate and having many holes; a heat emitting resistor formed on the second membrane and having many holes; a first membrane formed on the second membrane including the heat emitting resistor and having many holes; a sensing electrode formed on the first membrane and having many holes; and a sensing material formed on the sensing electrode.

16 Claims, 4 Drawing Sheets

(56) References Cited

U.S. PATENT DOCUMENTS

| | | | |
|---|---|---|---|
| 7,189,471 B2* | 3/2007 | Jankowksi et al. | 429/425 |
| 7,534,402 B2* | 5/2009 | Morse et al. | 422/198 |
| 8,286,478 B2* | 10/2012 | Speldrich | 73/204.23 |
| 2011/0165719 A1* | 7/2011 | Solzbacher et al. | 438/53 |
| 2012/0287962 A1* | 11/2012 | Ooishi | 374/37 |
| 2013/0259084 A1* | 10/2013 | Ooishi | 374/36 |

OTHER PUBLICATIONS

I. Elmi et al., "Development of Ultra-Low-Power Consumption MOX Sensors with Ppb-Level VOC Detection Capabilities for Emerging Applications", Sensors and Actuators B: Chemical, vol. 135, Sep. 9, 2008, pp. 342-351.

* cited by examiner

MICROELECTROMECHANICAL SYSTEMS TYPE SEMICONDUCTOR GAS SENSOR USING MICROHEATER HAVING MANY HOLES AND METHOD FOR MANUFACTURING THE SAME

CROSS-REFERENCE TO RELATED APPLICATIONS

This application is based on and claims priority from Korean Patent Application Nos. 10-2011-0011436, filed on Feb. 9, 2011, and 10-2011-0068818, filed on Jul. 12, 2011, with the Korean Intellectual Property Office, the present disclosure of which is incorporated herein in its entirety by reference.

TECHNICAL FIELD

The present disclosure relates to a semiconductor gas sensor, and more particularly, to a microelectromechanical systems type semiconductor gas sensor using a microheater having many holes and a method for manufacturing the same.

BACKGROUND

The research on a gas sensor has been conducted for a long period of time and various types of gas sensors have been commercialized at present. Among them, there is a gas sensor using a semiconductor sensing material. In the gas sensor using the semiconductor sensing material, when a gaseous component is adsorbed onto the surface of a semiconductor or reacts with adsorbed gas such as oxygen which was adsorbed in advance, electrons are transferred between adsorbed molecules and the semiconductor surface, and as a result, conductivity and surface potential of the semiconductor are changed. Since the degrees of the changes depend on the concentration and measurement temperature of sensed gas, the degrees are used for a gas sensing principle.

A semiconductor gas sensor can be mass produced due to a simple structure and an easy process and are mounted in a personal portable terminal or used in a ubiquitous sensor network to be used in various services due to a small size and low power consumption as compared with an optical gas sensor or an electrochemical gas sensor through measurement of conductivity by a spectrum or ion mobility of measured air.

The semiconductor gas sensor of the related art includes a bulk type semiconductor gas sensor with a sensing material, a sensing electrode, and a heater for increasing an operational temperature in order to improve a sensing characteristic on a substrate made of alumina or quartz, or an MEMS type semiconductor gas sensor that is similar to the above gas sensor in other parts but removes a part with the heater through a method such as etching to thermally separate the corresponding part to reduce power consumption.

The bulk type semiconductor gas sensor is resistant to a sudden impact, while the bulk type semiconductor gas sensor has large power consumption in order to maintain a high operational temperature for improving the sensing characteristic, such that it is difficult to apply the bulk type semiconductor gas sensor to a portable terminal or a sensor node for a ubiquitous sensor network (USN) service.

The existing MEMS type semiconductor gas sensor has still lower power consumption than the bulk type semiconductor gas sensor by etching a substrate (primarily silicon) of a heat emitting resistor part and thermally separating the corresponding part. The method therefore is divided into a bulk micromachining method of etching a rear substrate while membranes and the heat emitting resistor part remain and a surface micromachining method of etching only a part of the rear substrate while some of the membranes and the heat emitting resistor part remain.

In the former case, since the membranes are connected with the substrate without a hole, the membranes have relatively mechanical strength, but a portion having a size corresponding to the thickness of the substrate needs to be etched, and as a result, process cost is increased. In the latter case, since only a part of the thickness of the rear substrate is etched while some of the membranes and the heat emitting resistor part remain, the process cost is relatively low and the rear surface of the substrate is closed, and as a result, it is easy to handle elements, but since the membranes are connected with the substrate while the membranes have the holes, the membranes have a relatively weak structural characteristic. Therefore, both the structures are relatively weak to the sudden impact.

However, an MEMS type semiconductor gas sensor is required, which is structurally, mechanically, and electrically stable even with respect to the sudden impact while having lowest amount of power consumption in order to be used for various services with being mounted on the portable terminal or the ubiquitous sensor network.

SUMMARY

The present disclosure has been made in an effort to provide an MEMS type semiconductor gas sensor using a microheater having many holes, which is structurally, mechanically, and electrically stable in an MEMS semiconductor gas sensor that has a micro-size and power consumption which is remarkably reduced, and a method for manufacturing the same.

Further, the present disclosure has been made in an effort to provide an MEMS type semiconductor gas sensor using a microheater having many holes capable of providing a service under various environments and a method for manufacturing the same.

An exemplary embodiment of the present disclosure provides an MEMS type semiconductor gas sensor using a microheater having many holes, including: a substrate of which a central region is etched with a predetermined thickness; a second membrane formed at an upper portion of the central region of the substrate and having many holes; a heat emitting resistor formed on the second membrane and having many holes; a first membrane formed on the second membrane including the heat emitting resistor and having many holes; a sensing electrode formed on the first membrane and having many holes; and a sensing material formed on the sensing electrode.

Another exemplary embodiment of the present disclosure provides a method for manufacturing an MEMS type semiconductor gas sensor using a microheater having many holes, including: forming a second membrane at an upper portion of a central region of a substrate; forming a heat emitting resistor having many holes on the second membrane; forming a first membrane having many holes on the second membrane including the heat emitting resistor; forming a sensing electrode having many holes on the first membrane; forming a sensing material on the sensing electrode; patterning a region to be etched and forming many holes in the second membrane; and etching the substrate with a predetermined thickness through the region to be etched.

Yet another exemplary embodiment of the present disclosure provides a method for manufacturing an MEMS type semiconductor gas sensor using a microheater having many holes, including: forming a second membrane at an upper portion of a central region of a substrate; forming a heat emitting resistor having many holes on the second membrane; forming a first membrane having many holes on the second membrane including the heat emitting resistor; forming a sensing electrode having many holes on the first membrane; patterning a region to be etched and forming many holes in the second membrane; etching the substrate with a predetermined thickness through the region to be etched; and forming a sensing material on the sensing electrode.

As described above, according to the exemplary embodiments of the present disclosure, by providing the MEMS type semiconductor gas sensor using a microheater having many holes by drilling many holes in membranes and a heat emitting resistor part and overall or partially etching rear surfaces of the membranes and the heat emitting resistor with a predetermined thickness through this part to thermally separate the corresponding surfaces or support the membranes, and a method for manufacturing the same, a life-span of the sensor is increased by implementing both a bulk type semiconductor gas sensor and the MEMS type semiconductor gas sensor which has low power consumption and is structurally, mechanically, and electrically stable even with respect to a sudden impact, such as an MEMS type microheater implemented by the existing bulk or surface micromachining.

Further, according to the exemplary embodiments of the present disclosure, the MEMS type semiconductor gas sensor is mounted on various systems (for example, a portable terminal or a sensor node) to provide various services even under a lot of extreme environments.

In addition, the MEMS type semiconductor gas sensor according to the exemplary embodiments of the present disclosure can be used even in a limited battery capacity due to a low power characteristic for a long time and the MEMS type semiconductor gas sensor is stably driven even under various environments in which energy converting elements such as a thermoelectric element and a piezoelectric element operate, such that the MEMS type semiconductor gas sensor can be driven by using a self-charging power supply.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

Figure 1:
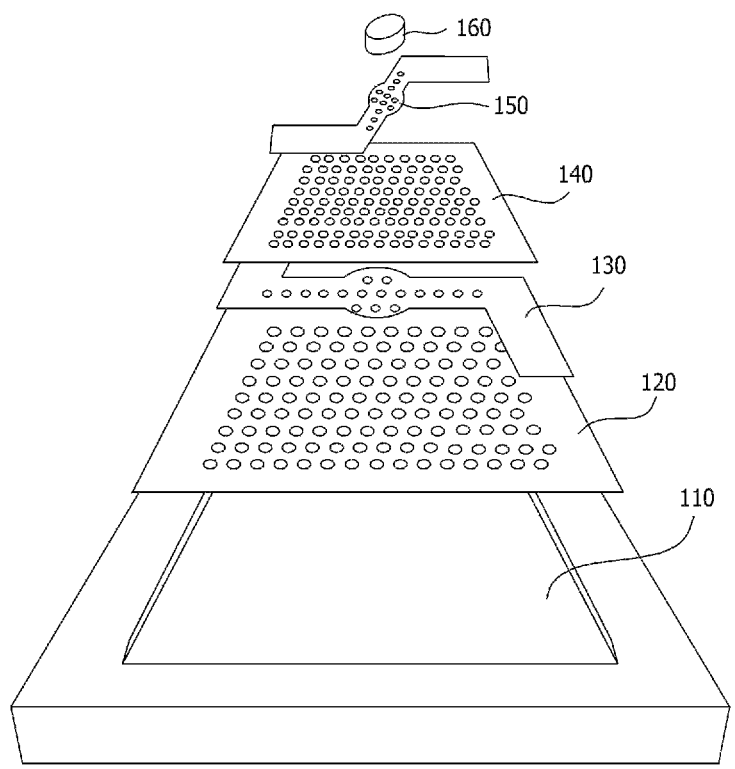
FIG. 1 is an exploded perspective view showing a configuration of an MEMS type semiconductor gas sensor using a microheater having many holes according to a first exemplary embodiment of the present disclosure.

FIG. 1 is an exploded perspective view showing a configuration of an MEMS type semiconductor gas sensor using a microheater having many holes according to a first exemplary embodiment of the present invention.

Referring to FIG. 1, a microelectromechanical systems (MEMS) type semiconductor gas sensor according to the first exemplary embodiment of the present disclosure includes a substrate 110 of which a central region is etched with a predetermined thickness, a second membrane 120 formed at an upper portion of the central region of substrate 110 and having many holes, a heat emitting resistor 130 formed on second membrane 120 and having many holes, a first membrane 140 formed on second membrane 120 including heat emitting resistor 130 and having many holes, a sensing electrode 150 formed on first membrane 140 and having many holes, and a sensing material 160 formed on sensing electrode 150.

As substrate 110, a silicon substrate used in a general semiconductor process may be used and a substrate doped with aluminum oxide ($Al_2O_3$), magnesium oxide (MgO), quartz, gallium-nitrogen (GaN), or gallium-arsenic (GaAs) may be used.

Second membrane 120 is constituted by a single or a plurality of silicon oxide films or silicon nitride films and may be formed through a thermal oxidation deposition method, a sputtering deposition method, or a chemical vapor deposition method. Second membrane 120 structurally serves to protect heat emitting resistor 130 when etching substrate 120 while supporting the microheater. Further, many holes are formed on second membrane 120 through a photolithography process and an etching process and the holes are used to etch substrate 110.

Heat emitting resistor 130 may be made of metals such as gold (Au), tungsten (W), platinum (Pt), and palladium (Pd), silicon, or a conductive metal oxide and may be formed on second membrane 120 in an inter-digital shape or a gap shape through a sputtering deposition method, an E-beam deposition method, or an evaporation deposition method. Further, many holes are formed on heat emitting resistor 130 through the photolithography process and the etching process and the holes are used to etch substrate 110. In addition, heat emitting resistor 130 may be connected with an external circuit (not shown) by a heater electrode pad and a bonding wire.

Meanwhile, in order to further improve an adhesive strength at the time of forming heat emitting resistor 130, an attachment layer (not shown) including chrome (Cr) or titanium (Ti) may be further formed between second membrane 120 and heat emitting resistor 130 through the sputtering deposition method, the E-beam deposition method, or the evaporation deposition method.

First membrane 140 is constituted by a single or a plurality of silicon oxide films or silicon nitride films and may be formed through the thermal oxidation deposition method, the sputtering deposition method, or the chemical vapor deposition method. First membrane 140 is positioned between heat emitting resistor 130 and sensing electrode 150 to electrically insulate both electrodes from each other and serves to structurally support the microheater. Further, many holes are formed on first membrane 140 through the photolithography process and the etching process and the holes are used to etch substrate 110.

Sensing electrode 150 is formed on first membrane 140 and specifically, a pair of electrodes is formed to pass through the central region of substrate 110. Sensing electrode 150 is made of a metal including at least one of platinum (Pt), aluminum (Al), and gold (Au) or the conductive metal oxide and may be formed through the sputtering deposition method, the E-beam deposition method, or the evaporation deposition method. Further, a bonding wire (not shown) for outputting variation in resistance value of sensing material 160 depending on adsorption and desorption of gas to the outside contacts both ends of sensing electrode 150.

Sensing material 160 as a gas sensing material for showing the variation in resistance by adsorbing gas may adopt materials such as a metal oxide, a carbon nano tube (CNT), and graphene and may be formed through a sol-gel method, a drop coating method, a screen printing method, the sputtering deposition method, or the chemical vapor deposition method.

Additionally, a protective layer (not shown) formed on sensing electrode 150 except for a region where the sensing material 160 is positioned and made of a material without conductivity may be further included. Herein, the protective layer (not shown) may be a silicon film or the silicon nitride film and may be formed through the thermal oxidation deposition method, the sputtering deposition method, or the chemical vapor deposition method.

The MEMS type semiconductor gas sensor using the microheater having many holes according to the exemplary embodiment of the present disclosure configured as above minimizes deformation of the membranes even under a sudden impact or a long driving environment while minimizing power consumption to thereby extend the life-span of the MEMS type semiconductor gas sensor and the MEMS type semiconductor gas sensor can operate under various environments.

Figure 2:
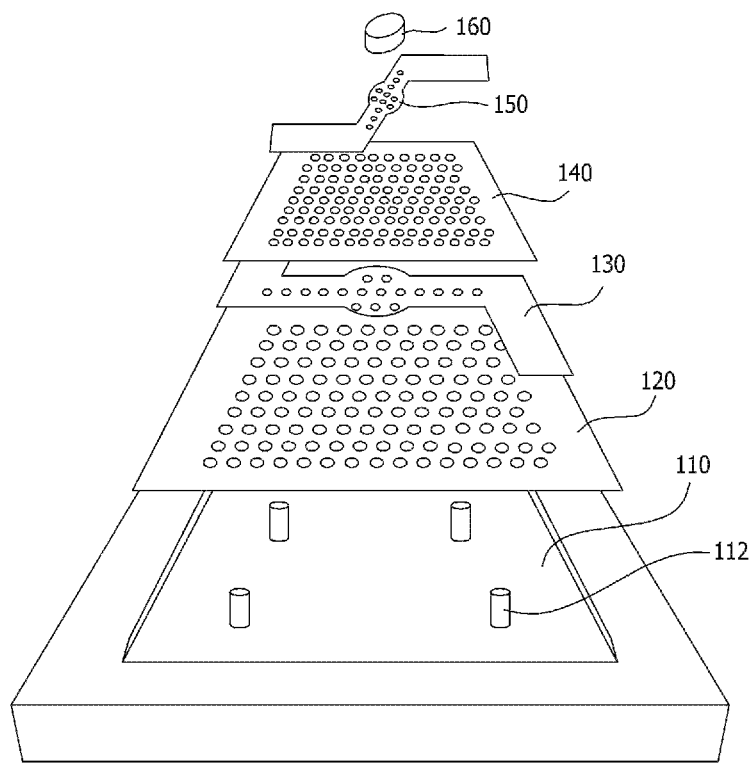
FIG. 2 is an exploded perspective view showing a configuration of an MEMS type semiconductor gas sensor using a microheater having many holes according to a second exemplary embodiment of the present disclosure.

FIG. 2 is an exploded perspective view showing a configuration of an MEMS type semiconductor gas sensor using a microheater having many holes according to a second exemplary embodiment of the present invention.

Referring to FIG. 2, the MEMS type semiconductor gas sensor using the microheater having many holes according to the second exemplary embodiment of the present disclosure can minimize deformation of membranes 120 and 140 even under a sudden impact or repeated operation and extend a life-span of the MEMS type semiconductor gas sensor by forming a column 112 supporting membranes 120 and 140 through remaining a part of substrate 110 at the time of etching substrate 110 below membranes 120 and 140, and heat emitting resistor 130.

FIGS. 3A to 3G are process flowcharts showing a method for manufacturing an MEMS type semiconductor gas sensor using a microheater having many holes according to an exemplary embodiment of the present disclosure.

Figure 3A:
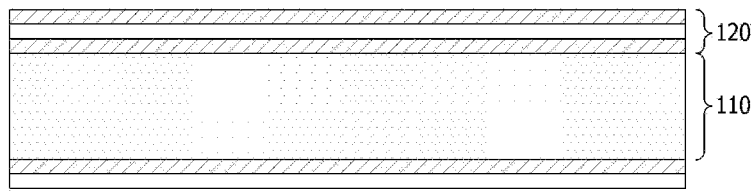
FIGS. 3A to 3G are process flowcharts showing a method for manufacturing an MEMS type semiconductor gas sensor using a microheater having many holes according to an exemplary embodiment of the present disclosure.

Referring to FIG. 3A, second membrane 120 is formed by depositing the single or the plurality of silicon oxide films or silicon nitride films on the upper portion of the central region of substrate 110 through the thermal oxidation deposition method, the sputtering deposition method, or the chemical vapor deposition method.

Figure 3B:
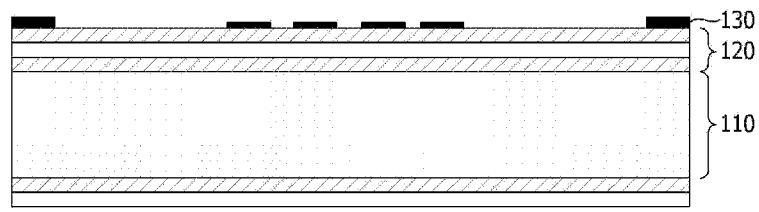

Referring to FIG. 3B, heat emitting resistor 130 is formed by depositing metallic films made of gold (Au), tungsten (W), platinum (Pt), and palladium (Pd), a silicon film, or a conductive metal oxide film on second membrane 120 through the sputtering deposition method, the E-beam deposition method, or the evaporation deposition method. Further, many holes are formed in heat emitting resistor 130 by patterning heat emitting resistor 130 through the photolithography process and the etching process.

Figure 3C:
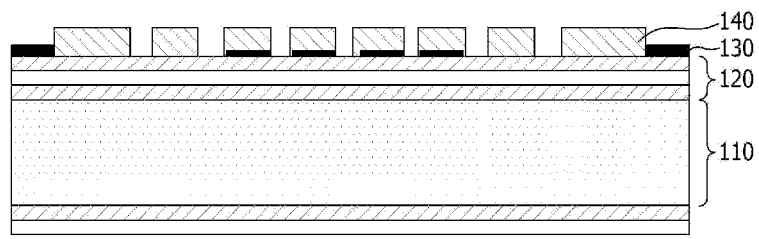

Referring to FIG. 3C, first membrane 140 is formed by depositing the single or the plurality of silicon oxide films or silicon nitride films on heat emitting resistor 130 through the thermal oxidation deposition method, the sputtering deposition method, or the chemical vapor deposition method. Further, many holes are formed in first membrane 140 by patterning first membrane 140 through the photolithography process and the etching process.

Figure 3D:
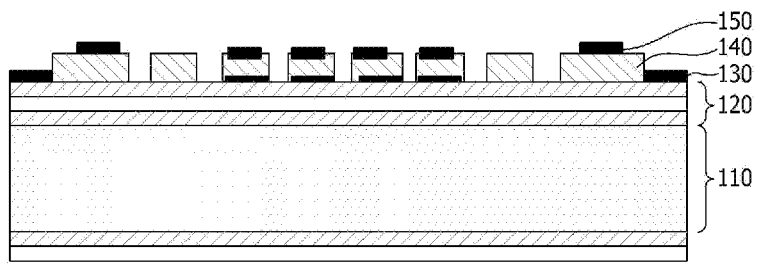

Referring to FIG. 3D, sensing electrode 150 is formed by depositing metallic films made of platinum (Pt), aluminum (Al), or gold (Au) or the conductive metal oxide on first membrane 140 through the sputtering deposition method, the E-beam deposition method, or the evaporation deposition method. Further, many holes are formed in sensing electrode 150 by patterning sensing electrode 150 through the photolithography process and the etching process.

Figure 3E:
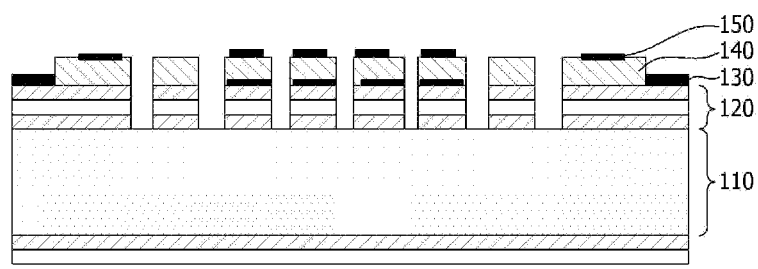

Meanwhile, in order to thermally separate membranes 120 and 140, and heat emitting resistor 130, substrate 110 is etched therebelow and as shown in FIG. 3E, a region to be etched is patterned in advance through the photolithography process and the etching process. In this case, many holes are formed in second membrane 120 at the same time. Accordingly, the region to be etched is formed and many holes are formed in second membrane 120 through one etching process to reduce the number of process times.

Figure 3F:
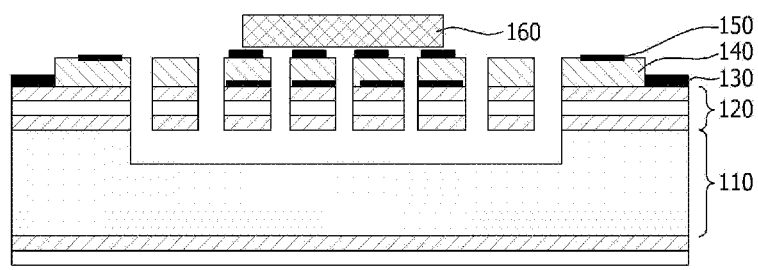

Referring to FIG. 3F, substrate 110 is etched with a predetermined thickness through the region to be etched. In this case, in order to etch a part which is not exposed by the hole, substrate 110 may be etched through an isotropic etching process using $XeF_2$ gas.

Figure 3G:
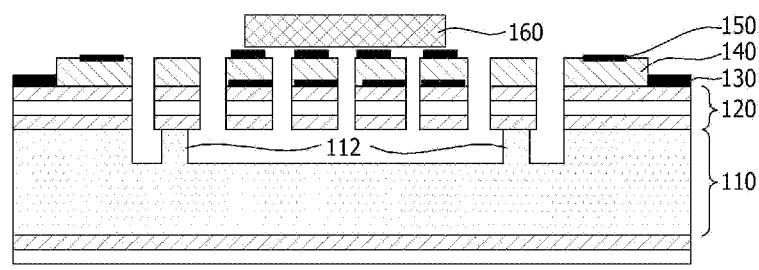

In the second exemplary embodiment of the present disclosure, as shown in FIG. 3G, when substrate 110 is etched, column 112 supporting membranes 120 and 140 is formed by remaining a part of substrate 110 to minimize deformation of membranes 120 and 140 even under the sudden impact or repeated operation and extend the life-span of the MEMS type semiconductor gas sensor.

Additionally, in a method for manufacturing the MEMS type semiconductor gas sensor using the microheater having many holes according to the exemplary embodiment of the present disclosure, sequences of a sensing material depositing process and a substrate etching process are changed depending on a deposition method of the sensing material.

For example, in the case of the sensing material depositing process in which pressure is applied to the substrate, such as a screen printing method, the sensing material is first formed and the substrate is etched with the predetermined thickness to manufacture the MEMS type semiconductor gas sensor.

In the case of the sensing material depositing process in which pressure is not applied to the substrate, such as the sol-gel method, the drop coating method, the sputtering deposition method, or the chemical vapor deposition method, the substrate is first etched with the predetermined thickness and the sensing material is formed later to manufacture the MEMS type semiconductor gas sensor.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An MEMS type semiconductor gas sensor using a microheater having many holes, comprising:
   a substrate of which a central region is etched with a predetermined thickness;

a second membrane formed at an upper portion of the central region of the substrate and having many holes;

a heat emitting resistor formed on the second membrane and having many holes;

a first membrane formed on the second membrane including the heat emitting resistor and having many holes;

a sensing electrode formed on the first membrane and having many holes; and a sensing material formed on the sensing electrode.

2. The MEMS type semiconductor gas sensor using a microheater having many holes of claim 1, further comprising a protective layer formed on a sensing electrode except for a region where the sensing material is positioned and made of a material without conductivity.

3. The MEMS type semiconductor gas sensor using a microheater having many holes of claim 1, wherein the substrate is a silicon substrate or any one of aluminum oxide ($Al_2O_3$), magnesium oxide (MgO), quartz, gallium-nitrogen (GaN), and gallium-arsenic (GaAs).

4. The MEMS type semiconductor gas sensor using a microheater having many holes of claim 1, wherein the first membrane and the second membrane are constituted by a single or a plurality of silicon oxide films or silicon nitride films.

5. The MEMS type semiconductor gas sensor using a microheater having many holes of claim 1, wherein the heat emitting resistor is metals including at least one of gold (Au), tungsten (W), platinum (Pt), and palladium (Pd), silicon, or a conductive metal oxide.

6. The MEMS type semiconductor gas sensor using a microheater having many holes of claim 1, wherein the heat emitting resistor is formed in an inter-digital shape or a gap shape.

7. The MEMS type semiconductor gas sensor using a microheater having many holes of claim 1, further comprising an attachment layer positioned between the second membrane and the heat emitting resistor to further improve an adhesive strength at the time of forming the heat emitting resistor.

8. The MEMS type semiconductor gas sensor using a microheater having many holes of claim 7, wherein the attachment layer includes chrome (Cr) or titanium (Ti).

9. The MEMS type semiconductor gas sensor using a microheater having many holes of claim 1, the sensing electrode outputs variation in resistance value of the sensing material depending on adsorption and desorption of gas to the outside.

10. The MEMS type semiconductor gas sensor using a microheater having many holes of claim 1, wherein the sensing electrode is constituted by metal including at least one of platinum (Pt), aluminum (Al), and gold (Au) or a conductive metal oxide.

11. The MEMS type semiconductor gas sensor using a microheater having many holes of claim 1, wherein the sensing material is any one of a metal oxide, a carbon nano tube (CNT), and graphene.

12. The MEMS type semiconductor gas sensor using a microheater having many holes of claim 1, wherein at least one column supporting the second membrane is formed in the etching region of the substrate.

13. A method for manufacturing an MEMS type semiconductor gas sensor using a microheater having many holes, comprising:

forming a second membrane at an upper portion of a central region of a substrate;

forming a heat emitting resistor having many holes on the second membrane;

forming a first membrane having many holes on the second membrane including the heat emitting resistor;

forming a sensing electrode having many holes on the first membrane;

forming a sensing material on the sensing electrode;

patterning a region to be etched and forming many holes in the second membrane; and etching the substrate with a predetermined thickness through the region to be etched.

14. The method of claim 13, wherein in the etching of the substrate with the predetermined thickness, at least one column supporting the second membrane is formed in an etching region.

15. A method for manufacturing an MEMS type semiconductor gas sensor using a microheater having many holes, comprising:

forming a second membrane at an upper portion of a central region of a substrate;

forming a heat emitting resistor having many holes on the second membrane;

forming a first membrane having many holes on the second membrane including the heat emitting resistor;

forming a sensing electrode having many holes on the first membrane;

patterning a region to be etched and forming many holes in the second membrane;

etching the substrate with a predetermined thickness through the region to be etched; and forming a sensing material on the sensing electrode.

16. The method of claim 15, wherein in the etching of the substrate with the predetermined thickness, at least one column supporting the second membrane is formed in an etching region.

* * * * *